(12) United States Patent
Okada

(10) Patent No.: US 7,435,230 B2
(45) Date of Patent: Oct. 14, 2008

(54) OBTAINED TISSUE EXTRACTOR AND BIOPSY FORCEPS

(75) Inventor: Tsutomu Okada, Tachikawa (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 11/410,489

(22) Filed: Apr. 25, 2006

(65) Prior Publication Data

US 2006/0189892 A1  Aug. 24, 2006

Related U.S. Application Data

(63) Continuation of application No. PCT/JP2004/014382, filed on Sep. 30, 2004.

(30) Foreign Application Priority Data

Feb. 3, 2004  (JP)  ............................. 2004-026567

(51) Int. Cl.
- *A61B 10/00* (2006.01)
- *A61B 17/32* (2006.01)
- *A61B 17/00* (2006.01)

(52) U.S. Cl. .................. 600/564; 606/167; 606/207

(58) Field of Classification Search ......... 600/562–565, 600/568; 606/167, 168, 207
See application file for complete search history.

(56) References Cited

U.S. PATENT DOCUMENTS

| 5,295,990 A | * | 3/1994 | Levin ........................ 600/564 |
| 5,573,546 A | * | 11/1996 | Nakao ........................ 606/205 |
| 2006/0258954 A1 | * | 11/2006 | Timberlake et al. ......... 600/564 |

FOREIGN PATENT DOCUMENTS

| JP | 11-76244 | 3/1999 |
| WO | WO 95/08946 A2 | 4/1995 |

* cited by examiner

*Primary Examiner*—Max Hindenburg
*Assistant Examiner*—Emily M Lloyd
(74) *Attorney, Agent, or Firm*—Scully, Scott, Murphy & Presser, P.C.

(57) ABSTRACT

An obtained tissue extractor is used in combination with a biopsy forceps. The biopsy forceps includes an elongate insertion portion to be inserted into a body, and a biopsy cup provided at a tip of the insertion portion, including a pair of cup bodies which obtains a living body tissue, and having holes communicating with the inside of the cup bodies. The obtained tissue extractor includes protrusions, and the protrusions enter the inside of the cup bodies from the holes of the cup bodies when the cup bodies are driven to open in a state set at the distal end of the insertion portion, in order to release the obtained tissue from the cup bodies.

13 Claims, 12 Drawing Sheets

OBTAINED TISSUE EXTRACTOR AND BIOPSY FORCEPS

CROSS-REFERENCE TO RELATED APPLICATIONS

This is a Continuation Application of PCT Application No. PCT/JP2004/014382, filed Sep. 30, 2004, which was published under PCT Article 21(2) in Japanese.

This application is based upon and claims the benefit of priority from prior Japanese Patent Application No. 2004-026567, filed Feb. 3, 2004, the entire contents of which are incorporated herein by reference.

BACKGROUND OF THE INVENTION

1. Field of the Invention

This invention relates to an obtained tissue extractor and a biopsy forceps to obtain a tissue specimen from a body.

2. Description of the Related Art

Conventional endoscopic forcipes include, for example, a biopsy forceps disclosed in Jpn. Pat. Appln. KOKAI Publication No. 11-76244. The biopsy forceps is used in a state inserted through a forceps channel of an endoscope, and has, at its tip, a pair of biopsy cups which are driven to open/close by a link mechanism operated by remote manipulation at hand. The biopsy forceps captures and obtains a tissue in the biopsy cups. After the tissue has been obtained, the tissue contained in the biopsy cups is extracted and used as a specimen, and the specimen is pathologically diagnosed.

BRIEF SUMMARY OF THE INVENTION

According to an aspect of the present invention, an obtained tissue extractor is used in combination with a biopsy forceps. The biopsy forceps includes an elongate insertion portion to be inserted into a body, and a biopsy cup provided at a tip of the insertion portion, including a pair of cup bodies which obtains a living body tissue, and having holes communicating with the inside of the cup bodies. The obtained tissue extractor includes protrusions, and the protrusions enter the inside of the cup bodies from the holes of the cup bodies when the cup bodies are driven to open in a state set at the distal end of the insertion portion, in order to release the obtained tissue from the cup bodies.

DETAILED DESCRIPTION OF THE INVENTION

A best mode for carrying out this invention will hereinafter be described in reference to the drawings.

First, a first embodiment will be described using FIGS. 1 to 6B.

Figure 1:
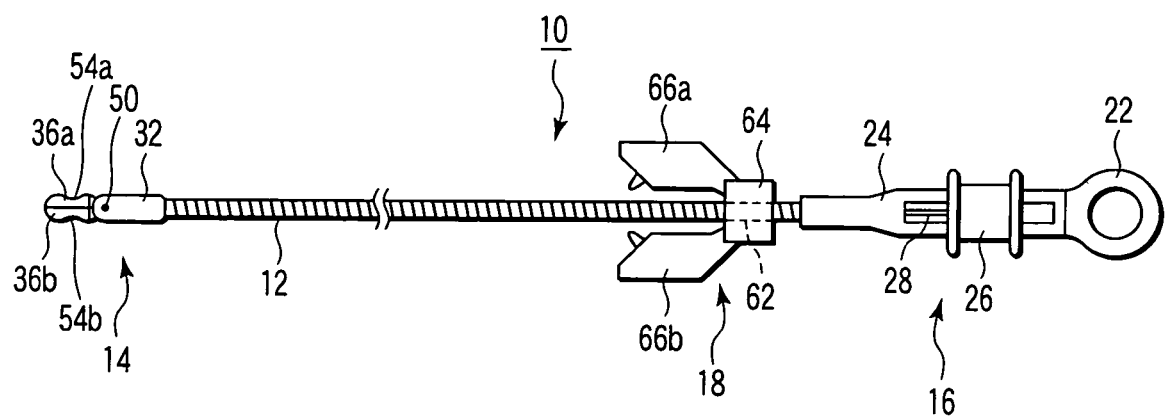
FIG. 1 is a schematic side view showing a biopsy forceps according to a first embodiment.

In FIG. 1, there is shown an endoscopic biopsy forceps 10 according to the first embodiment. The biopsy forceps 10 includes a flexible sheath 12, a treatment portion 14, an operation portion 16, and an obtained tissue extractor 18.

The flexible sheath 12 is an elongate insertion portion to be inserted into a body. The flexible sheath 12 is cylindrically formed to have moderate flexibility owing to a tightly wound coil.

The operation portion 16 is provided at a proximal end of the flexible sheath 12. The operation portion 16 includes an operation portion main body 24 which integrally has a finger hook ring 22 at a rear end thereof, and a slider 26 provided slidably on an outer peripheral surface of the operation portion main body 24 along the axial direction of the sheath 12. An operation wire 28 is provided inside the operation portion main body 24, and a rear end of the operation wire 28 is fixed to the slider 26. The operation wire 28 extends toward the treatment portion 14 through the inside of the flexible sheath 12.

Figure 2A:
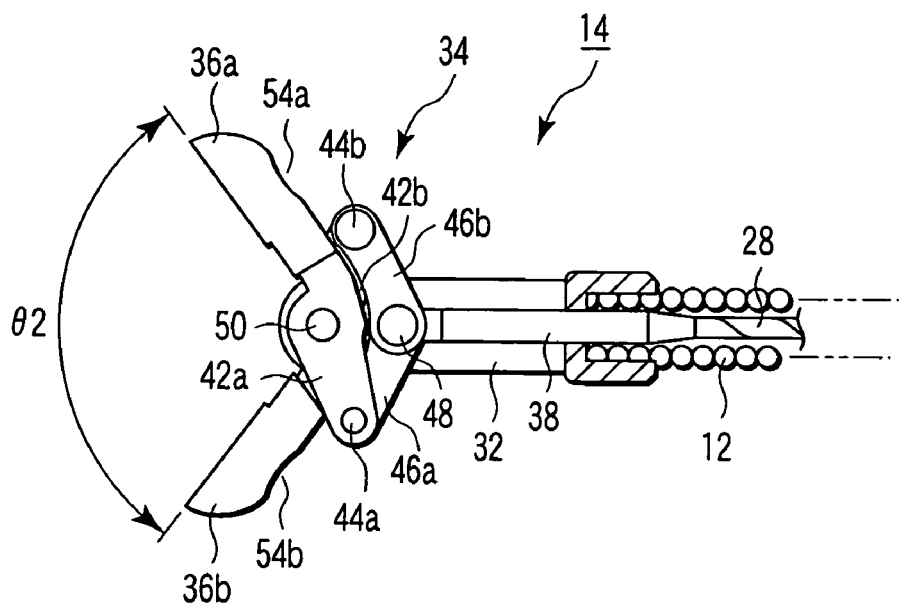
FIG. 2A is a schematic partial sectional view showing the configuration of a distal end of the biopsy forceps according to the first embodiment.

The treatment portion 14 is provided at a distal end of the flexible sheath 12. As shown in FIG. 2A, the treatment portion 14 includes a cylindrical support 32, a pantograph mechanism 34, and a pair of cup bodies 36a, 36b of a biopsy cup (forceps cup). The cup bodies 36a, 36b have the same shape.

The support 32 is integrally provided at the distal end of the sheath 12. Inside the support 32, a coupling member 38 integrally connected to a distal end of the operation wire 28 is provided movably along the axial direction of the sheath 12.

The pantograph mechanism 34 includes a pair of links 46a, 46b, and a first pin rod 48 which pivotally supports the links 46a, 46b at a distal end of the coupling member 38. The links 46a, 46b are fitted to be attached to rear extending arms 42a, 42b of the cup bodies 36a, 36b by support pins 44a, 44b, respectively. The rear extending arms 42a, 42b of the cup bodies 36a, 36b are supported pivotally with respect to each other on a second pin rod 50 provided at a distal end of the support 32. Thus, the second pin rod 50 is immobile with respect to the support 32. The first pin rod 48 moves forward and backward inside the support 32 by the forward and backward movement of the coupling member 38 with respect to the support 32. The support pins 44a, 44b protrude laterally from the support 32 if the first and second pin rods 48, 50 are brought into proximity.

As shown in FIG. 2A, the cup bodies 36a, 36b include receiving portions 52a, 52b which receive an obtained tissue, respectively. At the bottom of the receiving portions 52a, 52b of the cup bodies 36a, 36b, there are formed holes (openings) 54a, 54b, respectively, to prevent the tissue from being crushed when the tissue is cut off.

Figure 2B:
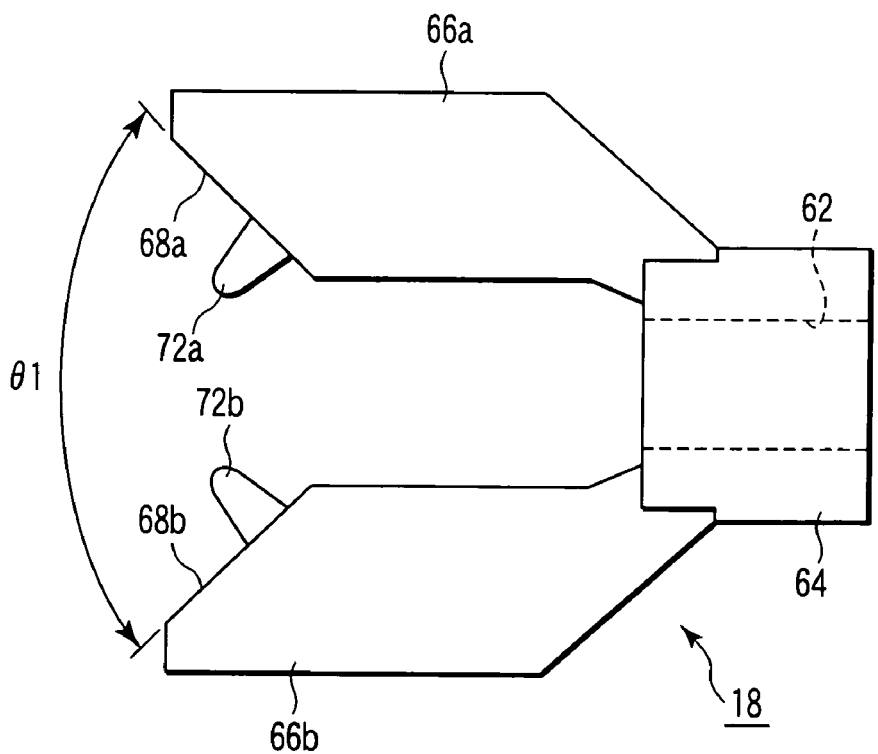
FIG. 2B is a side view of an obtained tissue extractor in the biopsy forceps according to the first embodiment.
Figure 3A:
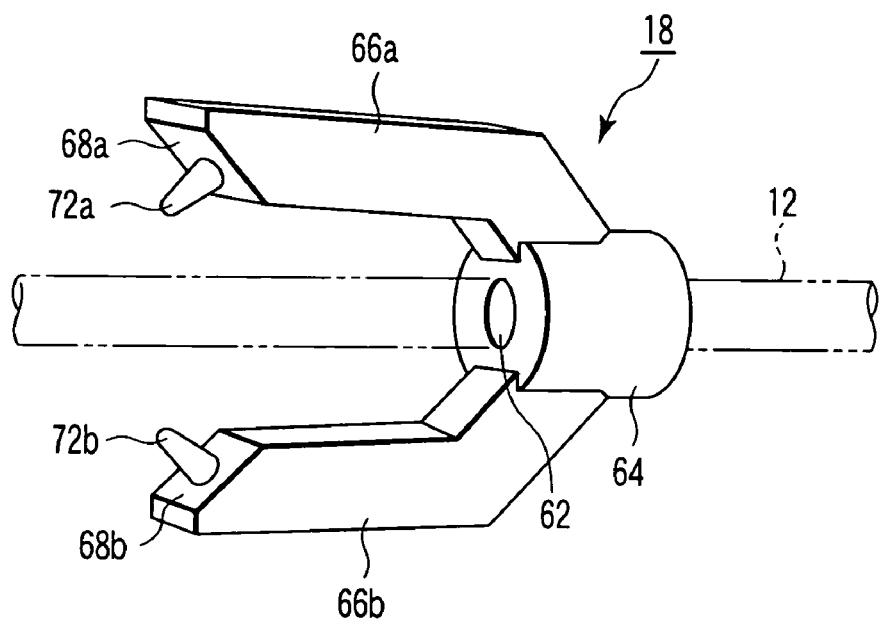
FIG. 3A is a schematic perspective view of the obtained tissue extractor slidably provided in a flexible sheath in the biopsy forceps according to the first embodiment.
Figure 3B:
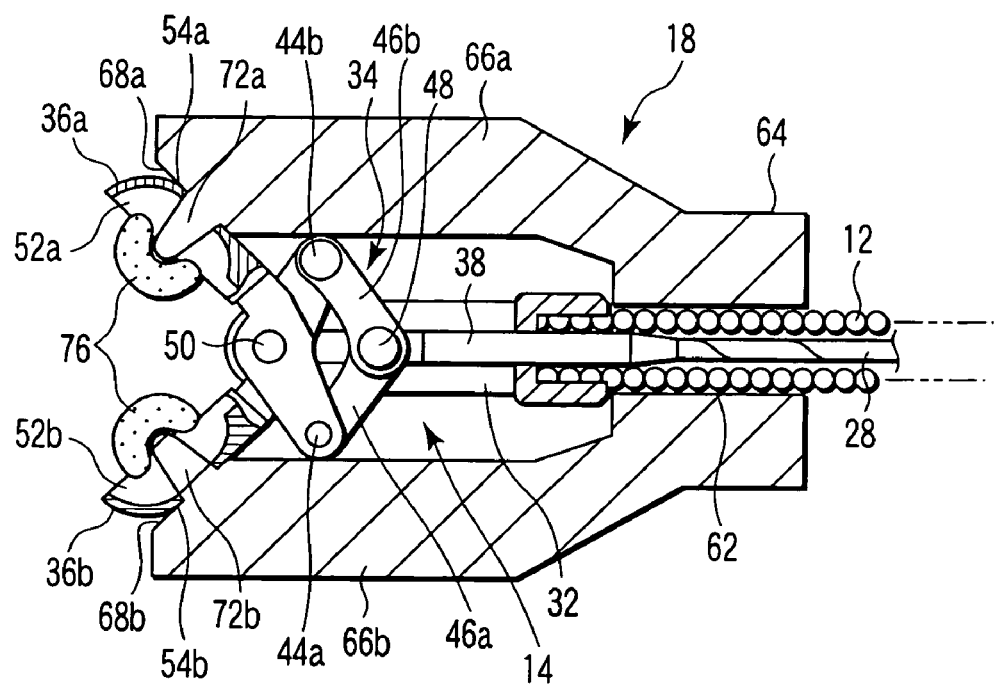
FIG. 3B is a schematic partial sectional view showing a state wherein the obtained tissue extractor of the biopsy forceps according to the first embodiment is used to release a living body tissue from a biopsy cup.

As shown in FIG. 1, the obtained tissue extractor 18 freely slides along the axial direction on an outer periphery of the flexible sheath 12. As shown in FIGS. 2B and 3A, the obtained tissue extractor 18 includes a cylindrical portion (main body) 64, and a pair of arms 66a, 66b. The cylindrical portion 64 includes a through-hole 62 through which the flexible sheath 12 is inserted and slidable. As shown in FIG. 3A, the pair of arms 66a, 66b extends forward from the cylindrical portion 64 with the flexible sheath 12 in between. Distal ends of the arms 66a, 66b are spaced out at a predetermined distance from the central axis of the through-hole 62 in parallel with each other. The predetermined distance at this point is a distance slightly larger than a distance between the support pins 44a, 44b of the pantograph mechanism 34 when the biopsy cup is opened at the maximum. Therefore, as shown in FIG. 3B, when the cup bodies 36a, 36b are opened so that the obtained tissue extractor 18 is in contact with the support 32, the support pins 44a, 44b of the pantograph mechanism 34 protruding on the lateral side of the support 32 are prevented from contacting inner walls of the arms 66a, 66b.

Planar portions 68a, 68b tilted with respect to the central axis of the obtained tissue extractor 18 are formed at distal ends of the arms 66a, 66b. The planar portions 68a, 68b are provided with protrusions (convex portions) 72a, 72b, respectively, which protrude vertically to the planar portions 68a, 68b and which are sized so that they are able to be inserted into the holes 54a, 54b of the cup bodies 36a, 36b. The protrusions 72a, 72b are formed in the planar portions 68a, 68b so that they enter the inside of the holes 54a, 54b when the cup bodies 36a, 36b are open. As shown in FIG. 2B, each of the planar portions 68a, 68b is tilted at an angle of $\theta_1/2$ with respect to the central axis of the obtained tissue extractor 18. The angle $\theta_1$ is formed to be substantially equal to or slightly smaller than an open angle $\theta_2$ (see FIG. 2A) of the cup bodies 36a, 36b. This ensures that the cup bodies 36a, 36b can be brought into contact with the planar portions 68a, 68b when the cup bodies 36a, 36b open. This therefore ensures that the obtained tissue is able to be removed.

Next, the operation of the biopsy forceps 10 having such a structure will be described.

The biopsy forceps 10 shown in FIG. 1 is inserted into a forceps channel of an unshown endoscope. At this point, the obtained tissue extractor 18 is disposed on a proximal side of the endoscope. The treatment portion 14 of the biopsy forceps 10 is brought into proximity of a living body tissue to be examined while the living body tissue is being observed by the endoscope. The thumb is put in the finger hook ring 22 of the operation portion main body 24 of the biopsy forceps 10, and the slider 26 is caught between the forefinger and the middle finger. In this state, the slider 26 is moved forward on the operation portion main body 24 with respect to the finger hook ring 22.

Then, the operation wire 28 moves forward with respect to the flexible sheath 12, such that the pantograph mechanism 34 is actuated. Thereby, the cup bodies 36a, 36b of the biopsy cup open with respect to each other. That is, due to the forward movement of the operation wire 28, the coupling member 38 moves forward with respect to the support 32, and the first pin rod 48 moves forward. Then, the links 46a, 46b pivot on the first pin rod 48 as a space between the first and second pin rods 48, 50 becomes smaller. Further, the rear extending arms 42a, 42b of the cup bodies 36a, 36b pivot on the support pins 44a, 44b. Thus, the cup bodies 36a, 36b open with respect to each other on the second pin rod 50 which is immobile with respect to the support 32.

Next, the biopsy forceps 10 is pressed against the tissue while the cup bodies 36a, 36b of the biopsy cup are open, and the slider 26 is moved back on the operation portion main body 24. Then, the cup bodies 36a, 36b close on the second pin rod 50 due to an action reverse to the above-mentioned action in opening the cup bodies 36a, 36b. A living body tissue 76 obtained at this moment is received in the receiving portions 52a, 52b of the cup bodies 36a, 36b. When the cup bodies 36a, 36b are completely closed, the biopsy forceps 10 is totally pulled, and the obtaining of the living body tissue 76 is completed. Then, the biopsy forceps 10 is pulled out of the channel of the endoscope.

The tissue 76 obtained by use of the biopsy forceps 10 is extracted as follows.

Figure 4A:
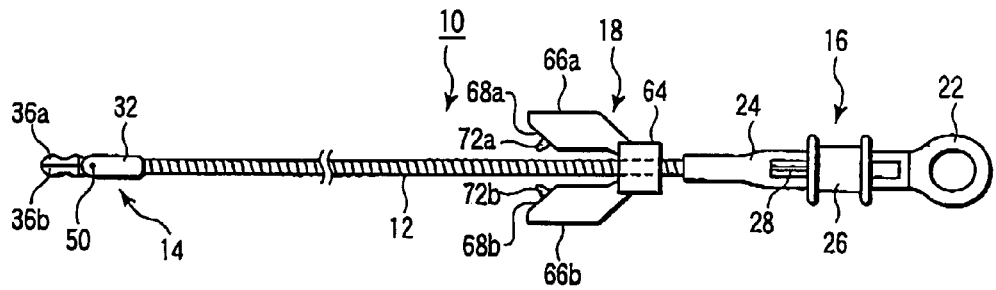
FIG. 4A is a schematic side view showing a state wherein the biopsy forceps is pulled out of a forceps channel of an endoscope after the living body tissue has been obtained by use of the biopsy forceps according to the first embodiment.
Figure 4B:
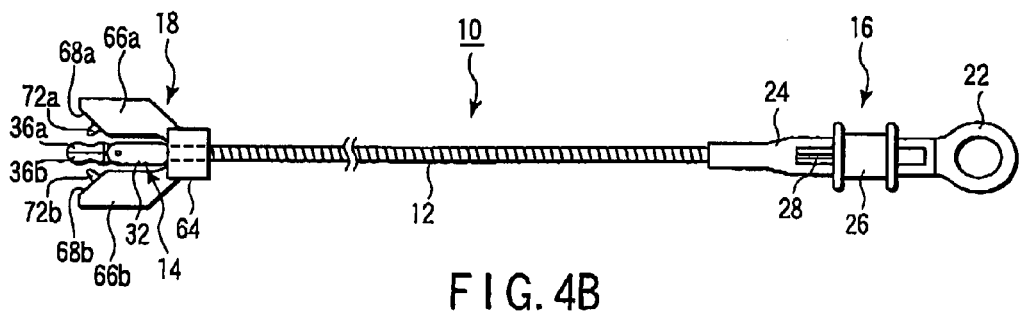
FIG. 4B is a schematic side view showing a state wherein the obtained tissue extractor is moved to a distal end side of an insertion portion after the living body tissue has been obtained by use of the biopsy forceps according to the first embodiment.

FIG. 4A shows the biopsy forceps 10 pulled out of the forceps channel of the endoscope. From the state shown in FIG. 4A, the cylindrical portion 64 of the obtained tissue extractor 18 is slid on the flexible sheath 12 to the side of the treatment portion 14, as shown in FIG. 4B. A distal end of the cylindrical portion 64 of the obtained tissue extractor 18 is brought into contact with a proximal end of the support 32.

Figure 4C:
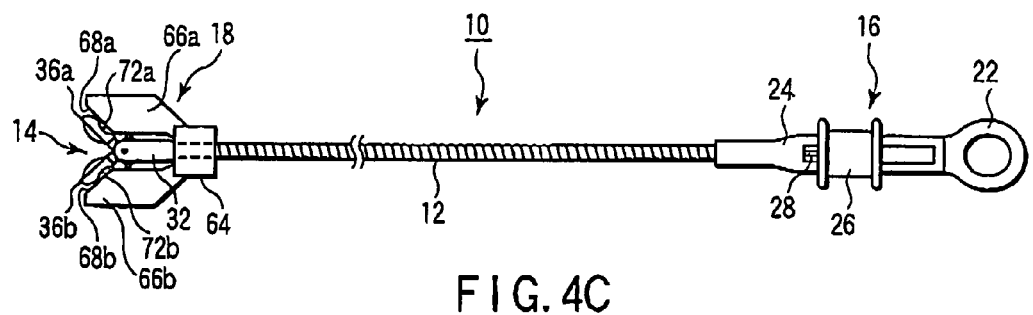
FIG. 4C is a schematic side view showing a state wherein after the living body tissue has been obtained by use of the biopsy forceps according to the first embodiment, the biopsy cup is opened, and then protrusions of the obtained tissue extractor are caused to enter holes of the biopsy cup to release the tissue.

In this state, the cup bodies 36a, 36b are opened, as shown in FIGS. 3B and 4C. The cup bodies 36a, 36b are brought into contact with the planar portions 68a, 68b of the obtained tissue extractor 18, and at the same time, the protrusions 72a, 72b of the obtained tissue extractor 18 enter the receiving portions 52a, 52b from the holes 54a, 54b of the cup bodies 36a, 36b. Consequently, the obtained tissue 76 in the receiving portions 52a, 52b is pushed out. That is, the obtained tissue 76 in the cup bodies 36a, 36b is easily extracted. The extracted tissue 76 is attached to a piece of filter paper as a specimen, put in a fixing solution such as formalin, and pathologically diagnosed.

As has been described above, the following can be said according to this embodiment.

The obtained tissue extractor 18 includes the protrusions 72a, 72b which enter the cup bodies 36a, 36b through the holes 54a, 54b from the outside of the cup bodies 36a, 36b when the cup bodies 36a, 36b are opened in a state positioned at the distal end of the flexible sheath 12 of the biopsy forceps 10. As a result, the tissue 76 obtained in the receiving portions 52a, 52b of the cup bodies 36a, 36b are able to be pushed out by the protrusions 72a, 72b and thus easily removed.

Figure 5A:
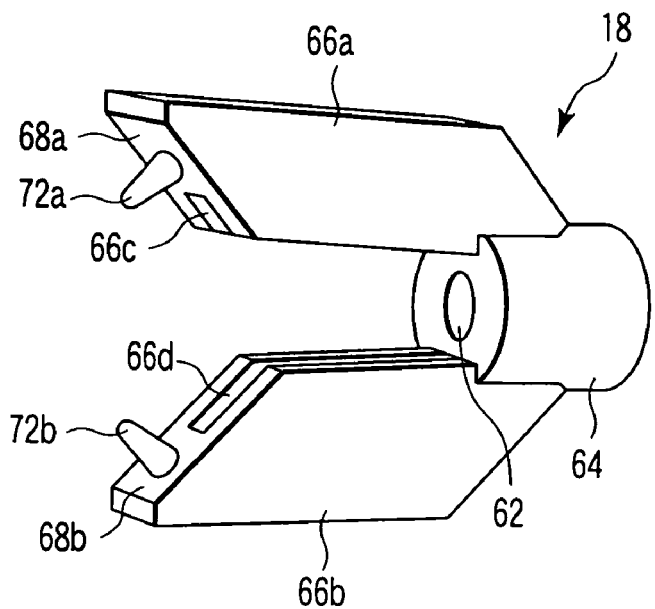
FIG. 5A is a schematic perspective view showing a state wherein slits capable of receiving part of a pantograph mechanism are formed in arms of the obtained tissue extractor in the biopsy forceps according to the first embodiment.

In this embodiment, as shown in FIG. 3B, opposite surfaces of the arms 66a, 66b of the collected tissue extractor 18 are spaced out in order to prevent the pantograph mechanism 34 from being brought into contact. Alternatively, as shown in FIGS. 5A and 5B, slits 66c, 66d may be formed in the opposite surfaces of the arms 66a, 66b of the obtained tissue extractor 18, respectively.

Figure 5B:
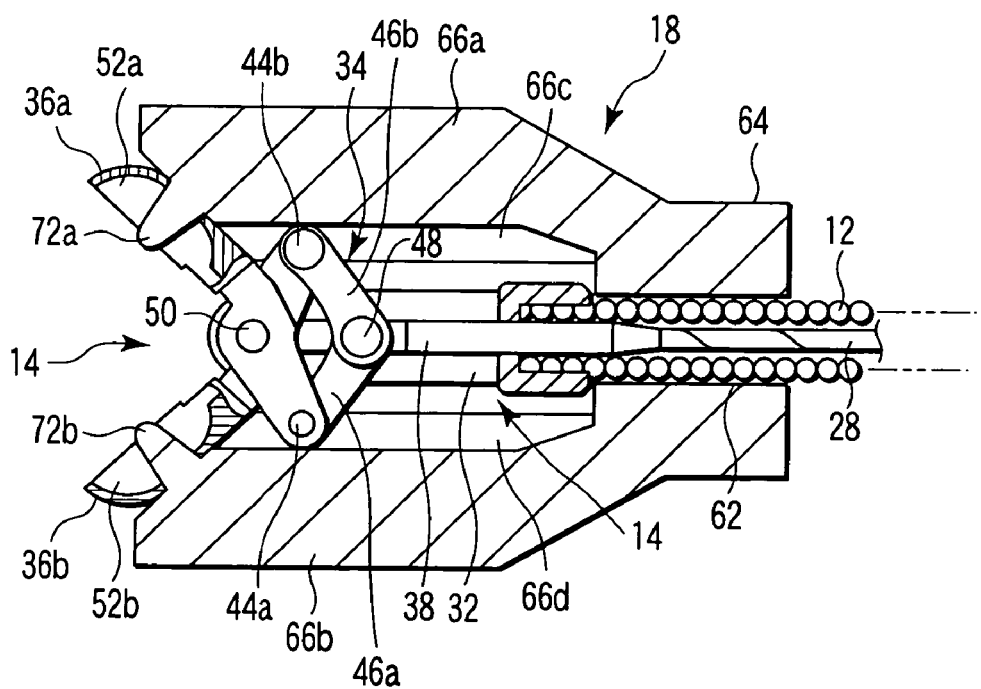
FIG. 5B is a schematic partial sectional view showing a state wherein the part of the pantograph mechanism is received in the slits formed in the arms of the obtained tissue extractor in the biopsy forceps according to the first embodiment.
Figure 6A:
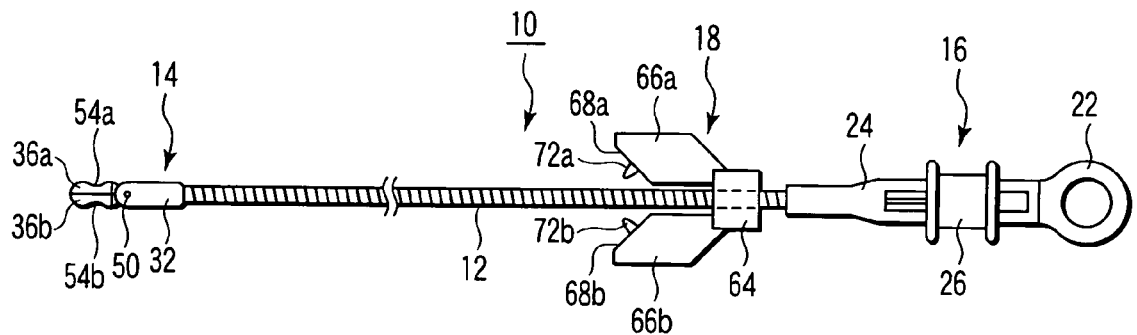
FIG. 6A is a schematic side view showing a state wherein the biopsy forceps is pulled out of the forceps channel of the endoscope after the living body tissue has been obtained by use of the biopsy forceps according to the first embodiment.
Figure 6B:
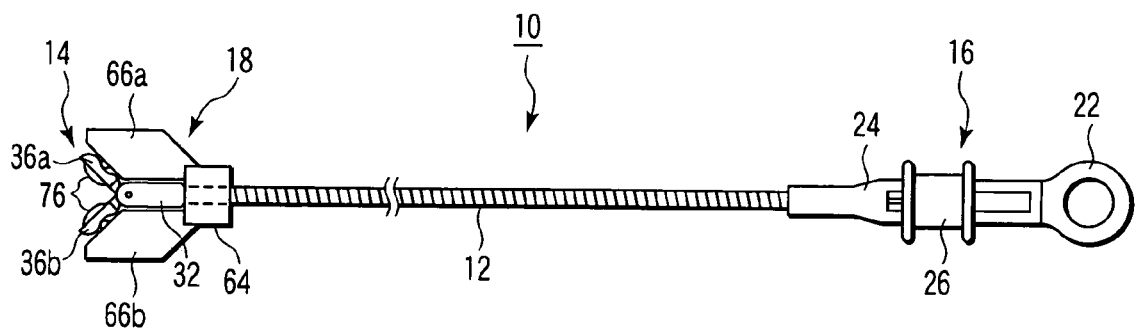
FIG. 6B is a schematic side view showing a state wherein after the living body tissue has been obtained by use of the biopsy forceps according to the first embodiment, the protrusion of the obtained tissue extractor is caused to enter the hole of the biopsy cup to release the tissue in a state where the biopsy cup is opened so that part of the pantograph mechanism is received in the slits of the obtained tissue extractor.

In this case, if the cup bodies 36a, 36b are opened when the obtained tissue extractor 18 is moved from the state shown in FIG. 6A to the state shown in FIG. 6B, the support pins 44a, 44b of the pantograph mechanism 34 protruding on the lateral side of the support 32 are received in the slits 66c, 66d (see FIG. 5B).

Next, a second embodiment will be described with FIGS. 7 to 9B. This embodiment is a modification of the first embodiment described above, and identical signs are assigned to members identical to, or having functions identical with, the members described in the first embodiment, and such members are not described in detail.

Figure 7:
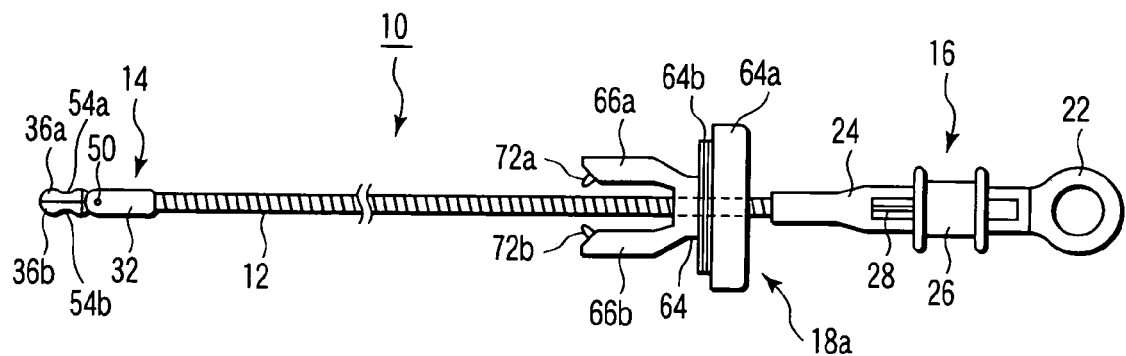
FIG. 7 is a schematic side view showing a biopsy forceps according to a second embodiment.
Figure 8:
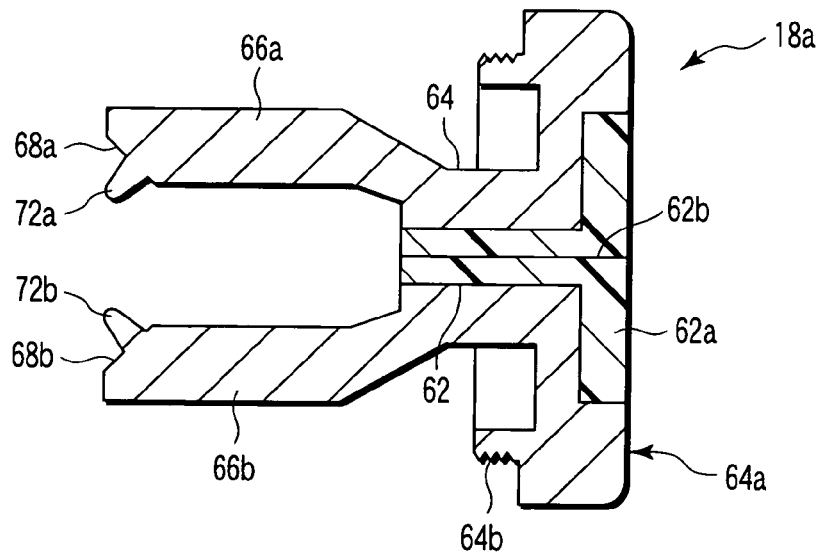
FIG. 8 is a longitudinal sectional view of obtained tissue extractor in the biopsy forceps according to the second embodiment.

In a biopsy forceps 10 of this embodiment, a proximal end of the obtained tissue extractor 18 described in the first embodiment is structured differently from an obtained tissue extractor 18a in this embodiment. As shown in FIGS. 7 and 8, a disk-shaped cover 64a is integrally formed at a proximal end of a cylindrical portion 64 of the obtained tissue extractor 18a in this embodiment.

As shown in FIG. 8, the cover 64a of the obtained tissue extractor 18a has, on its distal end side (protrusions 72a, 72b side), a fitting portion 64b which fits in a collection bottle 84 described later. An elastic rubber 62a is provided in the through-hole 62. In this rubber 62a, a slit 62b is formed so that the treatment portion 14 and the flexible sheath 12 are able to be inserted therethrough in a close contact state. The slit 62b is closed and sealed after the flexible sheath 12 and the treatment portion 14 are removed.

Next, the operation of the biopsy forceps 10 having such a structure will be described.

Figure 9A:
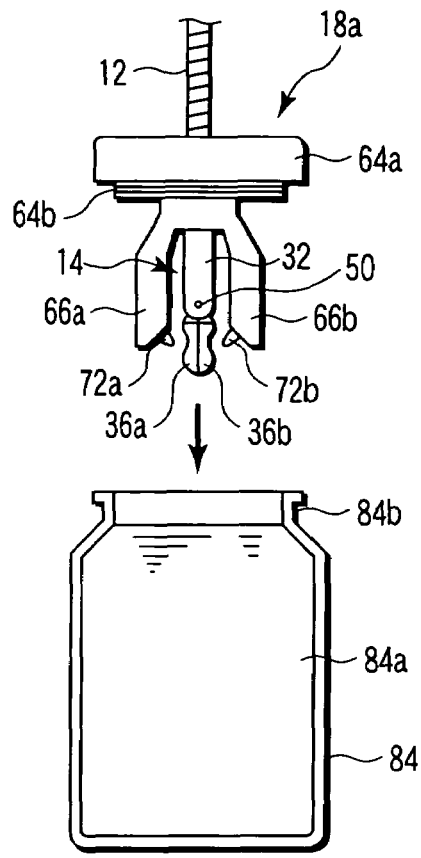
FIG. 9A is a schematic view showing a state wherein arms of the obtained tissue extractor are inserted into a tissue collection bottle filled with a fixing solution in a state where the obtained tissue extractor in the biopsy forceps according to the second embodiment is disposed at a distal end of an insertion portion.

A tissue is obtained by use of the biopsy forceps 10, and the biopsy forceps 10 is pulled out of a channel of an endoscope. Then, as shown in FIG. 9A, the obtained tissue extractor 18a is moved forward along the flexible sheath 12 to bring the rubber 62a into contact with a proximal end of a support 32. In that state, the treatment portion 14 and the obtained tissue extractor 18a are put into the collection bottle 84 filled with a fixing solution 84a such as formalin, and the fitting portion 64b of the cover 64a is fitted in an opening 84b of the collection bottle 84.

Figure 9B:
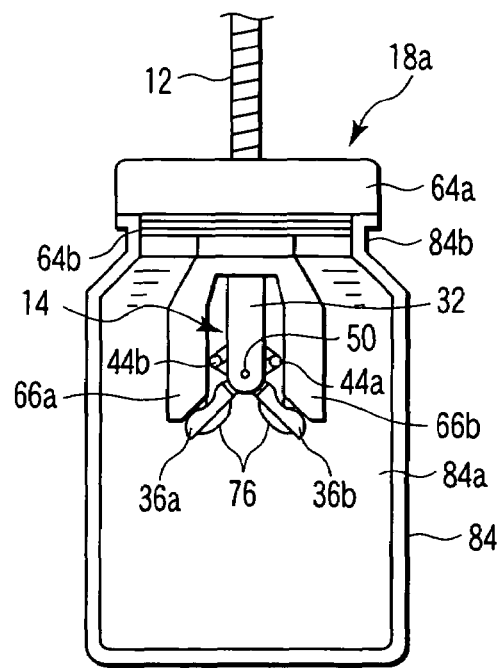
FIG. 9B is a schematic view showing a state wherein the obtained tissue extractor in the biopsy forceps according to the second embodiment is used as a cover and fixed on the tissue collection bottle, and a living body tissue is released from a biopsy cup.

In this state, as shown in FIG. 9B, the cup bodies 36a, 36b are opened. The protrusions 72a, 72b of the obtained tissue extractor 18a enter the receiving portions 52a, 52b of the cup bodies 36a, 36b through the holes 54a, 54b. Thus, the obtained tissue 76 is pushed out. In that state, if the collection bottle 84 is lightly shaken, the obtained tissue 76 drops in the fixing solution 84a. The cup bodies 36a, 36b are closed, and the biopsy forceps 10 is pulled out of the obtained tissue extractor 18a. The collection bottle 84 is sealed by the fitting portion 64b and the rubber 62a. The obtained tissue 76 in each of the collection bottles 84 is pathologically diagnosed.

As has been described above, the following can be said according to this embodiment.

After being easily dropped in the fixing solution 84a of the collection bottle 84, the obtained tissue 76 can be pathologically diagnosed in a state where the cover 64a is disposed in the collection bottle 84. Therefore, the obtained tissue 76 pushed out of the cup bodies 36a, 36b does not need to be taken out on filter paper or the like.

Next, a third embodiment will be described with FIGS. 10 to 14B. This embodiment is a modification of the first embodiment described above, and identical signs are assigned to members identical to, or having functions identical with, the members described in the first embodiment, and such members are not described in detail.

Figure 10:
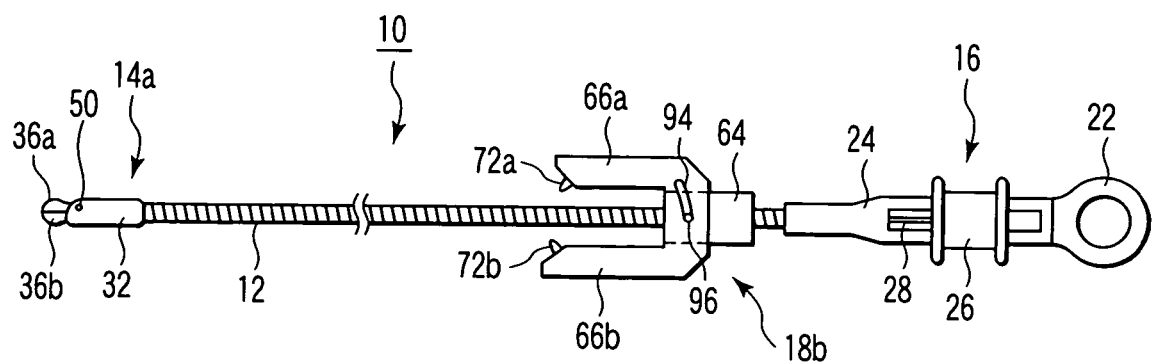
FIG. 10 is a schematic side view showing a biopsy forceps according to a third embodiment.

As shown in FIG. 10, an obtained tissue extractor 18b is disposed on an outer periphery of a flexible sheath 12 of a biopsy forceps 10 so that it can (slidably) move forward and backward along the axial direction of the flexible sheath 12.

Figure 11:
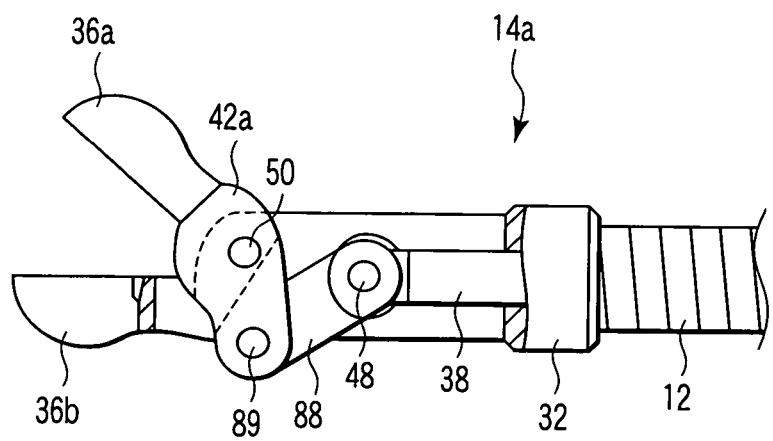
FIG. 11 is a schematic side view showing a treatment portion of the biopsy forceps according to the third embodiment.

As shown in FIG. 11, a treatment portion 14a of the biopsy forceps 10 in this embodiment is formed in a single swinging type. In this treatment portion 14a, a cup body 36b is immobile because it is fixed to the distal end of a support 32, and one cup body 36a only opens/closes with respect to the cup body 36b.

The treatment portion 14a includes, inside the support 32, a link 88 movable with respect to a coupling member 38 and coupled to a first pin rod 48, and a rear extending arm 42a of the one cup body 36a coupled to the link 88 by a support shaft 89. The rear extending arm 42a is supported on an immobile second pin rod 50 of the support 32. The other cup body 36b is fixed at the distal end of the support 32.

Thus, due to the forward and backward movement of an operation wire 28 (see FIG. 3B), the coupling member 38 moves forward and backward, the link 88 pivots on a first pin rod 48, and the rear extending arm 42a pivots on the second pin rod 50. Then, the one cup body 36a opens/closes with respect to the other cup body 36b.

Figure 12A:
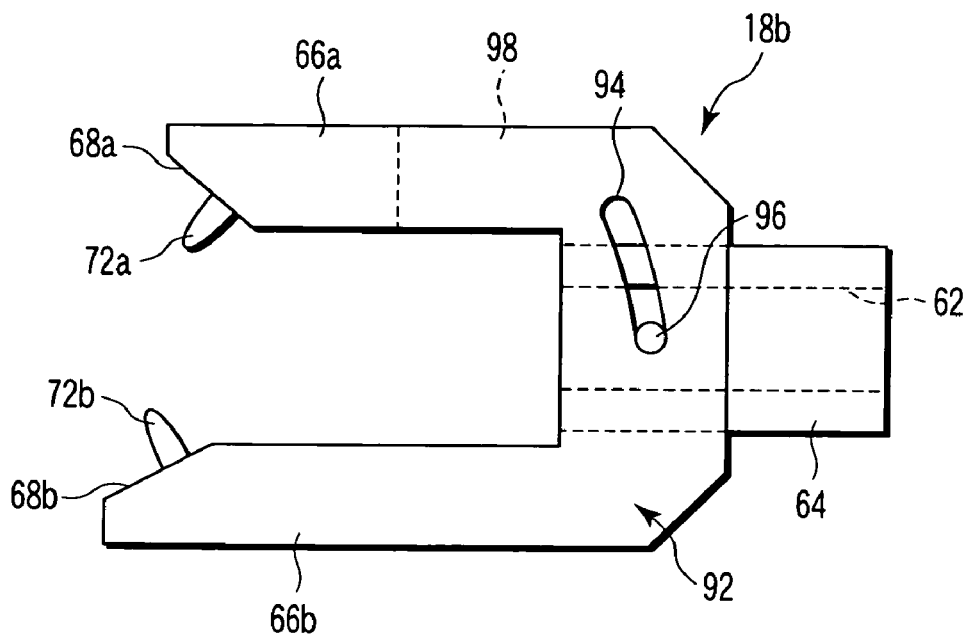
FIG. 12A is a schematic side view showing an obtained tissue extractor in the biopsy forceps according to the third embodiment.
Figure 12B:
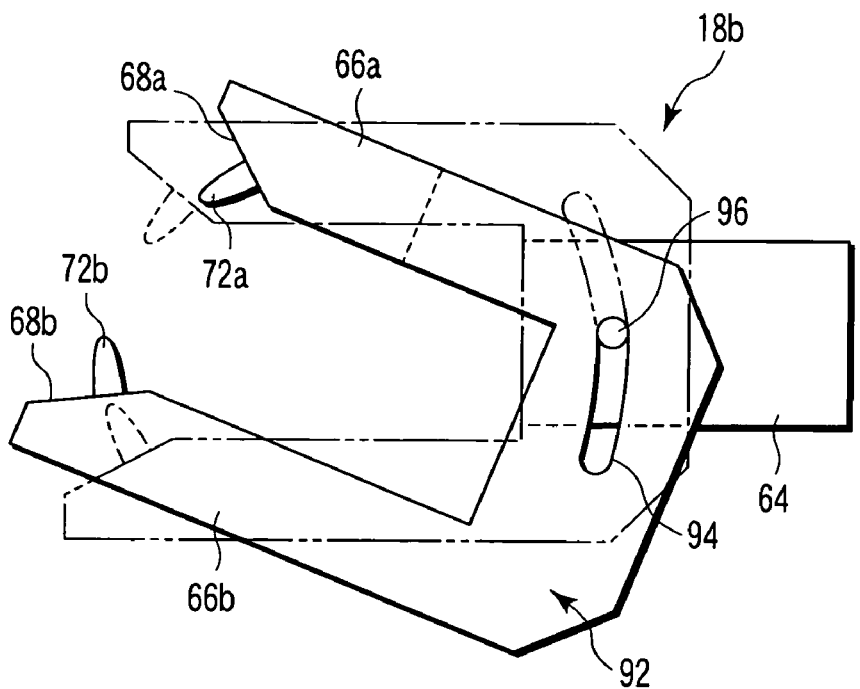
FIG. 12B is a schematic side view showing a state wherein a U-shaped portion is tilted with respect to a cylindrical portion of the obtained tissue extractor in the biopsy forceps according to the third embodiment.
Figure 13:
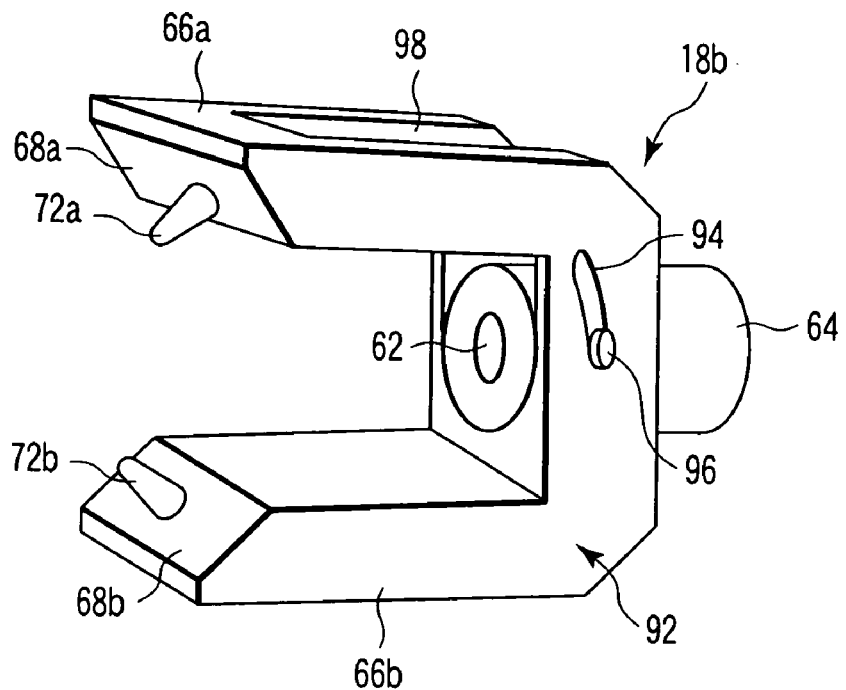
FIG. 13 is a schematic perspective view of the obtained tissue extractor in the biopsy forceps according to the third embodiment.

As shown in FIGS. 12A and 13, the obtained tissue extractor 18b has the following configuration. The obtained tissue extractor 18b includes a cylindrical portion 64, and a U-shaped member 92 including a pair of arms 66a, 66b having protrusions 72a, 72b. The cylindrical portion 64 is separate from the U-shaped member 92. A guide groove 94 is formed at a base of the arm 66a of the U-shaped member 92. On an outer surface of the cylindrical portion 64, an engagement pin 96 is formed which is movable in a state engaged in the guide groove 94. The engagement pin 96 provided in the cylindrical portion 64 is engaged with the guide groove 94. Thus, the engagement pin 96 moves along the guide groove 94. Therefore, as shown in FIG. 12B, the U-shaped member 92 can incline with respect to the cylindrical portion 64. It is to be noted that a clearance 98 is formed in the arm 66a to prevent the cylindrical portion 64 from contacting during inclining.

Next, the operation of the biopsy forceps 10 having such a structure will be described.

Figure 14A:
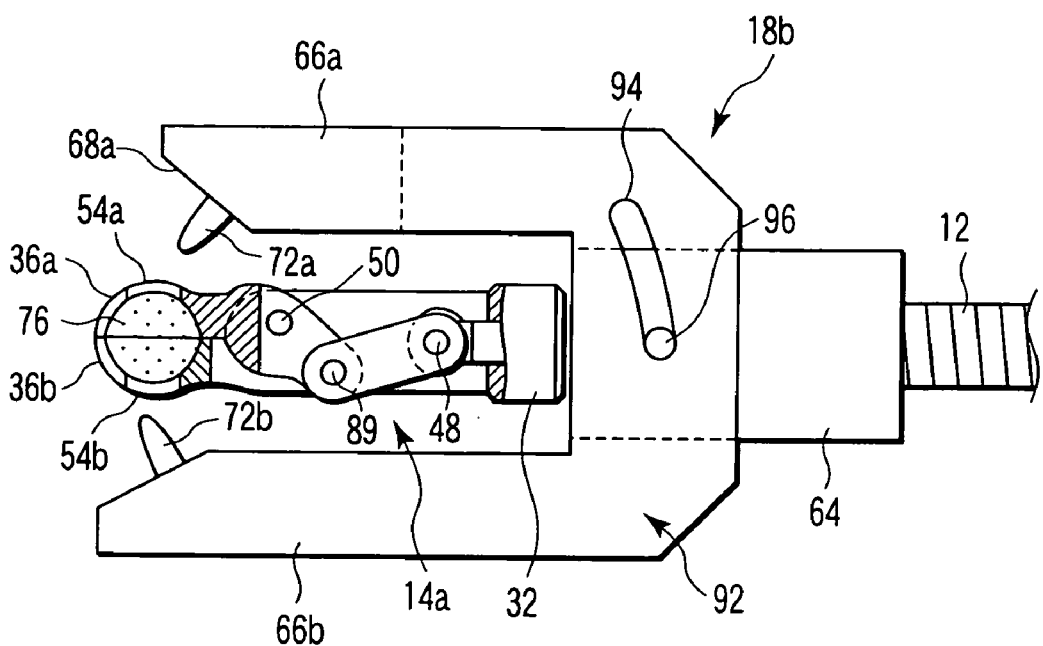
FIG. 14A is a schematic partial sectional view showing a state wherein the obtained tissue extractor is disposed at a distal end of an insertion portion after a tissue has been obtained by use of the biopsy forceps according to the third embodiment.

The biopsy forceps 10 is operated to obtain a tissue 76, and the biopsy forceps 10 is pulled out of the channel of the endoscope. Then, as shown in FIG. 14A, the obtained tissue extractor 18b is moved forward to bring the cylindrical portion 64 into contact with the proximal end of the support 32.

Figure 14B:
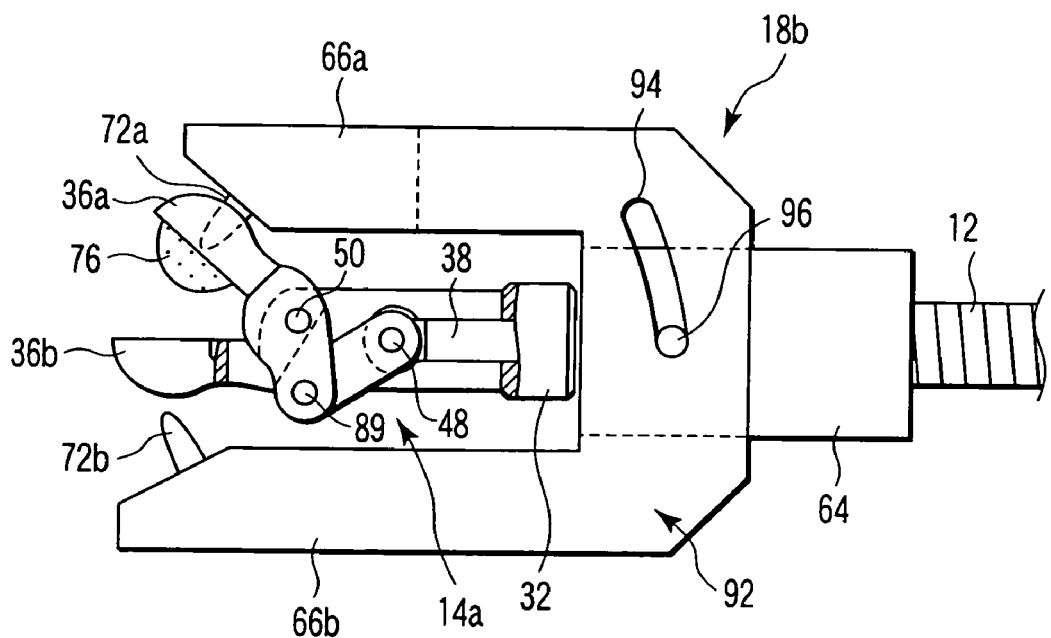
FIG. 14B is a schematic partial sectional view showing a state wherein after the tissue has been obtained in a biopsy cup by use of the biopsy forceps according to the third embodiment, the biopsy cup is opened so that a protrusion of one arm enters a hole of one cup body in a state where the obtained tissue extractor is disposed at the distal end of the insertion portion.

In this state, as shown in FIG. 14B, the operation portion 16 is operated to open the one cup body 36a with respect to the other cup body 36b. The one cup body 36a bumps into the planar portion 68a of the obtained tissue extractor 18b, and the protrusion 72a enters a receiving portion 52a of the cup body 36a through a hole 54a. Thus, the obtained tissue 76 is pushed out of the one cup body 36a.

Figure 14C:
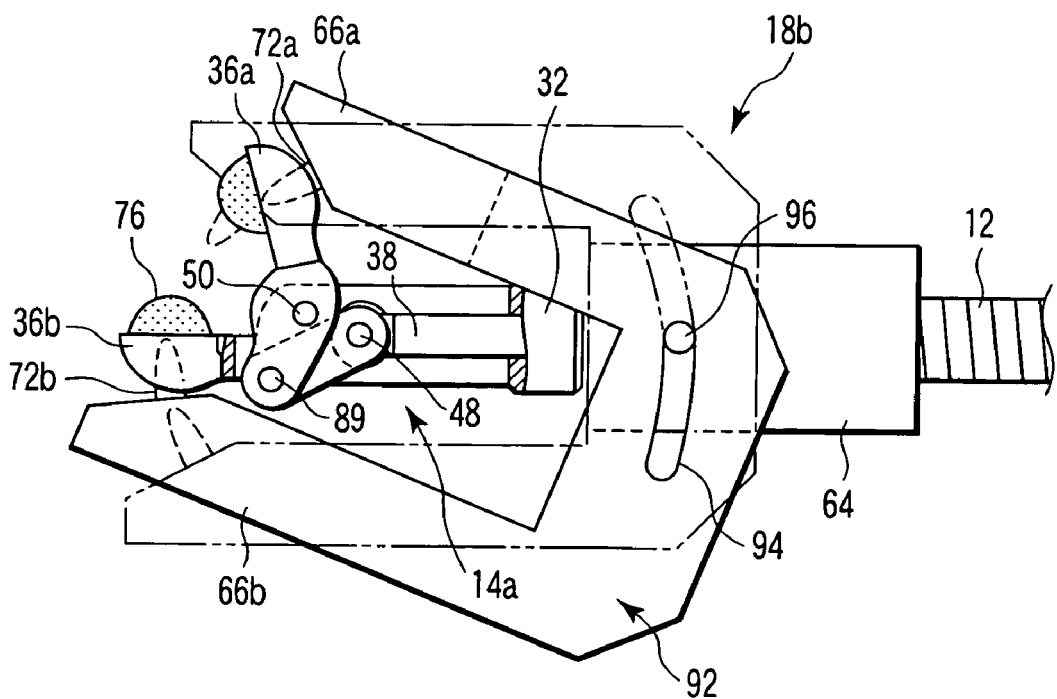
FIG. 14C is a schematic partial sectional view showing a state wherein after the tissue has been obtained in the biopsy cup by use of the biopsy forceps according to the third embodiment, the biopsy cup is opened so that the protrusion of one arm enters the hole of one cup body in a state where the obtained tissue extractor is disposed at the distal end of the insertion portion, and then the U-shaped portion is tilted with respect to the cylindrical portion of the obtained tissue extractor by force to open the cup body so that a protrusion of the other arm enters a hole of the other cup body.

Furthermore, when the one cup body 36a is opened, the engagement pin 96 is moved along the guide groove 94 of the U-shaped member 92 by drive force to open the cup body 36b, as shown in FIG. 14C. That is, the U-shaped member 92 inclines around the engagement pin 96, and the arm 66b is lifted such that the protrusion 72b enters the receiving portion 52b through the hole 54b of the other immobile cup body 36b. Thus, the obtained tissue 76 is pushed out of the other cup body 36b.

As has been described above, the following can be said according to this embodiment.

It is possible to easily extract even the tissue 76 obtained in the pair of cup bodies 36a, 36b of the single swinging biopsy cup. That is, it is also possible to push out and extract the obtained tissue 76 from the immobile cup body 36b.

A cover 64a (see FIG. 9A) may be attached to the proximal end of the cylindrical portion 64 described above. In this manner, the obtained tissue is taken into a collection bottle 84 owing to the function identical with the function described in the second embodiment.

While several embodiments have been specifically described above referring to the drawings, this invention is not limited to the embodiments described above, and includes all embodiments implemented without departing from the spirit thereof.

According to this invention, it is possible to provide an obtained tissue extractor and a biopsy forceps which make it easier to extract a tissue when extracting the tissue from a biopsy cup after the tissue has been obtained in the biopsy cup.

What is claimed is:

1. An obtained tissue extractor which is used in combination with a biopsy forceps, the biopsy forceps comprising:
   an elongated insertion portion to be inserted into a body;
   a biopsy cup provided at a distal end of the insertion section, including a pair of cup bodies at least one of which is able to be opened/closed and which are configured to obtain a living body tissue, and having holes communicating with the inside of the cup bodies; and
   a link mechanism configured to drive the biopsy cup to open/close by remote manipulation at a proximal end of the insertion portion,
   wherein the obtained tissue extractor is able to extract the obtained tissue from the biopsy cup, and the obtained tissue extractor comprises protrusions entering the inside of the cup bodies from the holes of the cup bodies when the cup bodies are driven to open in a position at the distal end of the insertion portion, in order to release the obtained tissue from the cup bodies, and
   the obtained tissue extractor further comprising:
   a cylindrical main body through which the insertion portion of the biopsy forceps is inserted; and
   a pair of arms extending toward the biopsy cup from the main body and having the protrusions provided at distal ends thereof.

2. The obtained tissue extractor according to claim 1, wherein the protrusions are arranged on a pair of planes tilted with respect to a central axis of the obtained tissue extractor, and
   an angle made by the pair of planes is formed to be at least one of an angle equal to an open angle of the cup bodies of the biopsy forceps when opened at the maximum and an angle smaller than the open angle.

3. The obtained tissue extractor according to claim 1, wherein
   the protrusions protrude from the pair of planes tilted with respect to a central axis of the main body, and
   the pair of planes is tilted at at least one of an open angle of the biopsy cup when opened and an angle smaller than the open angle.

4. The obtained tissue extractor according to claim 1, wherein the main body is able to be attached to and detached from the biopsy forceps.

5. The obtained tissue extractor according to claim 1, wherein at opposite positions of the arms, there are formed slits to receive the link mechanism which partially protrude when the biopsy cup of the biopsy forceps is open.

6. A biopsy forceps comprising:
   an elongate insertion portion to be inserted into a body;
   a biopsy cup provided at a distal end of the insertion portion, including a pair of cup bodies at least one of which is able to be opened/closed and which are configured to obtain a living body tissue, and including holes communicating with the inside of the cup bodies;
   a link mechanism configured to drive the biopsy cup to open/close by remote manipulation;
   an obtained tissue extractor having protrusions, the protrusions being slidably provided in the insertion portion, and entering the inside of the cup bodies through the holes of the cup bodies when the cup bodies are driven to open in a position at the distal end of the insertion portion, in order to release the obtained tissue from the cup bodies, a cylindrical main body through which the insertion portion of the biopsy forceps is inserted; and a pair of arms extending toward the biopsy cup from the main body and having the protrusions provided at distal ends thereof.

7. The biopsy forceps according to claim 6, wherein the biopsy cup is a single swinging type, the biopsy cup including a first cup fixed to the distal end of the insertion portion and a second cup being able to be opened and closed with respect to the first cup.

8. A biopsy forceps comprising:

an elongate insertion portion to be inserted into a body;

a biopsy cup provided at a distal end of the insertion portion, including a pair of cup bodies, only one of which is able to be opened/closed, and which are configured to obtain a living body tissue, and including holes communicating with the inside of the cup bodies;

a link mechanism configured to drive the biopsy cup to open/close by remote manipulation; and an obtained tissue extractor having protrusions, the protrusions being slidably provided in the insertion portion, and entering the inside of the cup bodies though the holes of the cup bodies when the cup bodies are driven to open in a position at the distal end of the insertion portion, in order to release the obtained tissue from the cup bodies, the tissue extractor being movable along the insertion portion;

a cylindrical main body through which the insertion portion of the biopsy forceps is inserted; and a pair of arms inclinably attached to the main body and having the protrusions provided at distal ends thereof, and the obtained tissue extractor comprises, in the main body and the arms, inclination mechanisms whereby the arms incline with respect to the main body by an operation of opening the cup bodies;

wherein the biopsy cup is a single swinging type, the biopsy cup including a first cup fixed to the distal end of the insertion portion and a second cup being able to be opened and closed with respect to the first cup.

9. The biopsy forceps according to claim 8, wherein the inclination mechanisms comprise:

a pin provided on an outer peripheral surface of the main body; and a guide groove which is provided in the arm and with which the pin is engaged.

10. The biopsy forceps according to claim 8, wherein the main body comprises a cover having a function of covering a collection container which collects the obtained tissue obtained by the biopsy cup.

11. The biopsy forceps according to claim 10, wherein the main body is provided with an elastic member movable along the insertion portion when the insertion portion of the biopsy forceps is inserted therethrough and having a slit which is sealed when the biopsy forceps is removed.

12. An obtained tissue extractor, which is used in combination with a biopsy forceps, the biopsy forceps comprising:

an elongated insertion portion to be inserted into a body;

a biopsy cup provided at a distal end of the insertion section, including a pair of cup bodies at least one of which is able to be opened/closed and which are configured to obtain a living body tissue, and having holes communicating with the inside of the cup bodies;

a link mechanism configured to drive the biopsy cup to open/close by remote manipulation at a proximal end of the insertion portion, a cylindrical main body inserted movably along the insertion portion of the biopsy forceps; and a pair of arms extending toward the biopsy cup from the main body and having the protrusions provided at distal ends thereof;

wherein the obtained tissue extractor is able to extract the obtained tissue from the biopsy cup, and the obtained tissue extractor comprises protrusions entering the inside of the cup bodies from the holes of the cup bodies when the cup bodies are driven to open in a position at the distal end of the insertion portion, in order to release the obtained tissue from the cup bodies; and wherein the main body comprises a cover having a function of covering a collection container which collects the obtained tissue obtained by the biopsy cup.

13. The obtained tissue extractor according to claim 12, wherein the main body is provided with an elastic member movable along the insertion portion when the insertion portion of the biopsy forceps is inserted therethrough and having a slit which is sealed when the biopsy forceps is removed.

* * * * *